United States Patent [19]

Togawa et al.

[11] Patent Number: 5,212,393
[45] Date of Patent: May 18, 1993

[54] SAMPLE CELL FOR DIFFRACTION-SCATTERING MEASUREMENT OF PARTICLE SIZE DISTRIBUTIONS

[75] Inventors: Yoshiaki Togawa; Tatsuo Igushi, both of Kyoto; Koichiro Matsuda, Otsu, all of Japan

[73] Assignee: Horiba, Ltd., Kyoto, Japan

[21] Appl. No.: 926,556

[22] Filed: Aug. 6, 1992

Related U.S. Application Data

[63] Continuation of Ser. No. 671,496, Mar. 19, 1991.

[30] Foreign Application Priority Data

Mar. 19, 1990 [JP] Japan ................. 2-71674

[51] Int. Cl.$^5$ ............................ G01N 15/06
[52] U.S. Cl. .................. 250/573; 250/574; 356/336; 356/338; 356/340
[58] Field of Search ............ 250/573, 574; 356/335, 356/336, 338, 341, 343, 340

[56] References Cited

U.S. PATENT DOCUMENTS

| | | | |
|---|---|---|---|
| 3,381,135 | 4/1968 | Keller | 250/573 |
| 3,557,376 | 1/1971 | Senyk | 250/573 |
| 3,562,535 | 2/1971 | Leger, Jr. | 250/573 |
| 3,701,620 | 10/1972 | Berkman et al. | 356/340 |
| 3,807,875 | 4/1974 | Fischer et al. | 250/573 |
| 4,371,786 | 2/1983 | Kramer | 250/573 |
| 4,391,129 | 7/1983 | Trinh et al. | 250/573 |
| 4,710,643 | 12/1987 | Schmukler et al. | 250/573 |
| 4,906,094 | 3/1990 | Ashida | 356/336 |

FOREIGN PATENT DOCUMENTS

| | | |
|---|---|---|
| 2833389 | 7/1989 | Australia . |
| 0029662 | 10/1980 | European Pat. Off. . |
| 0104661 | 9/1983 | European Pat. Off. . |
| 63-168033 | 7/1988 | Japan . |
| 8701451 | 10/1986 | PCT Int'l Appl. . |
| 2095827A | 10/1982 | United Kingdom . |

OTHER PUBLICATIONS

Review of Scientific Instruments, vol. 55, No. 9, Sep. 1984, pp. 1375-1400, New York, NY, US; J. A. Steinkamp: "Flow Cytometry" FIG. 5.

Primary Examiner—Jack I. Berman
Assistant Examiner—Kiet T. Nguyen
Attorney, Agent, or Firm—Price, Gess & Ubell

[57] ABSTRACT

A sample cell for use in measuring the particle size distribution of samples using diffraction-scattering measurement methods has a radiating surface which is beveled to increase the angle of incidence of scattered light which is scattered at a large scattering angle such that it is transmitted through the radiating surface of the sample cell and thereby allowed to impinge upon a detector.

15 Claims, 2 Drawing Sheets

SAMPLE CELL FOR DIFFRACTION-SCATTERING MEASUREMENT OF PARTICLE SIZE DISTRIBUTIONS

This is a continuation of application Ser. No. 671,496, filed on Mar. 19, 1991 for a SAMPLE CELL FOR DIFFRACTION-SCATTERING MEASUREMENT OF PARTICLE SIZE DISTRIBUTIONS.

FIELD OF THE INVENTION

The present invention relates to the diffraction-scattering measurements of samples and, more particularly, to a sample cell used in measuring the particle size distribution of samples in a diffraction-scattering measurement and testing apparatus.

BACKGROUND OF THE INVENTION

A conventional apparatus for making diffraction-scattering measurements of the particle size distribution of a sample is shown in FIG. 4. As shown therein, a laser beam 1 is projected into a square cylindrical sample cell 2' which contains a sample to be measured.

The sample cell 2' has a square external cross-section and an internal space $2a'$. The internal space $2a'$ of the sample cell 2' is continuously supplied with the sample liquid from an ultrasonic diffusion bath (not shown) by means of a circulating pump (not shown).

Laser beam 1 is transmitted into and through the sample cell 2', and scattered (diffracted) by particulates contained within the sample liquid in the sample cell's internal space $2a'$. The scattered light 5 radiating from the sample cell 2' is transmitted through a condenser lens 3, which collects the scattered light 5 and focuses the scattered light 5 upon the detector 4. The detector 4 may be a silicon photodiode.

Thus, the incident laser light 1 is scattered (diffracted) by the particles within the sample liquid, and the scattering or diffraction pattern 5 is directed onto the detector 4 for measurement. In this way it is possible to determine the particle size distribution of the particles within the sample liquid by measuring the intensity of the pattern of the scattered light 5.

A further depiction of the conventional sample cell 2' may be seen in FIGS. 5A and 5B. Therein, a particular light beam 1' from the laser beam 1 is scattered by a particle 6 within sample liquid in the sample cell 2'. The scattered light 5, 5', which is diffracted by the particle 6, is directed towards the rear surface of the sample cell $2b'$.

When the particle 6 scatters the light 5 at a small scattering angle $\Theta_1$, the scattered light 5 is refracted through the sample cell and is allowed to impinge upon the detector 4 by passing through the rear surface $2b'$ of the sample cell 2'. As an example, when the disbursion medium is water, light which is scattered at a scattering angle $\Theta_1$ less than approximately 50 degrees will be transmitted through a rear surface $2b'$, which is normal to the original angle of incidence.

On the other hand, when the particle 6 causes scattered light 5' to have a larger scattering angle $\Theta_2$, the scattered light 5' interacts with the rear surface of the sample cell $2b'$ at a minimal angle of incidence $\phi_2$. Since the angle $\phi_2$ is minimal, the scattered light 5' is not transmitted through the rear surface $2b'$, but is reflected from that surface, and is not allowed to reach the detector 4.

Thus, in conventional cells as depicted in FIGS. 4 and 5, when a particle 6 causes light to be scattered at large scattering angles $\Theta_2$, the scattered light 5' is fully reflected by the surface $2b'$ without any transmission. This causes the diffraction-scattering measurement to be an erroneous representation of the overall particle size distribution within the sample. In general, where the disbursion medium is water, any particle 6 producing a scattering angle $\Theta$ greater than or equal to approximately 50 degrees will produce reflected scattered light yielding an erroneous measurement.

The scattering angle is generally inversely proportional to the particle size; the smaller the particle, the larger the scattering angle. Thus, in a conventional apparatus for measuring the distribution of particle size, the particle sizes of particulates having reduced particle diameters have been difficult to measure, and the measurement of the particle size distribution over a wide range has proven to be impossible with a conventional sample cell.

OBJECTS OF THE INVENTION

It is therefore an object of the present invention to provide an apparatus for diffraction-scattering measuring the particle size distribution of particulates in a sample.

It is yet a further object of the present invention to provide an apparatus for measuring the particle size distribution of particles having a wide range of sizes.

It is yet a still further object of the present invention to provide a sample cell for use in diffraction-scattering measurements of particle size distribution which allows the scattered light component from larger particulates to be measured.

It is yet a still further object of the present invention to provide a sample cell for use in making diffraction-scattering measurements of particle size distributions of samples, which sample cell allows the measurement of particulates having reduced particle diameters with high accuracy, and allows the measurement of the distribution of particle sizes over a wide range by a relatively simple device.

SUMMARY OF THE INVENTION

These and other objects are provided in the present invention by a sample cell for use in a particle size distribution measurement apparatus using diffraction-scattering measurement methods. The sample cell allows a wide range of particle size distributions to be measured, by providing a beveled outer surface on the radiating or exit side of the sample cell, and thereby allowing scattered light from smaller particles to be transmitted to detectors.

By providing a beveled radiating or exit surface on the outer surface of the sample cell, the angle between the scattered light and the outer surface of the sample cell can be substantially increased so that scattered light having a large scattering angle is allowed to pass to the detector. By beveling the outer or exit surface, the angle of incidence between the scattered light and the outer surface of the sample cell is increased enough to allow transmission and eliminate reflection. This allows a more accurate measurement of the particle size distribution over a greater range of particle diameters.

BRIEF DESCRIPTION OF THE DRAWINGS

The objects and features of the present invention, together with further objects and advantages, may be understood by reference to the following drawings.

DETAILED DESCRIPTION OF THE PREFERRED EMBODIMENTS

The following description is provided to enable any person skilled in the art to make and use the invention and sets forth the best modes contemplated by the inventor[s] of carrying out the invention. Various modifications, however, will remain readily apparent to those skilled in the art, since the generic principles of the present invention have been defined herein.

Figure 1A:
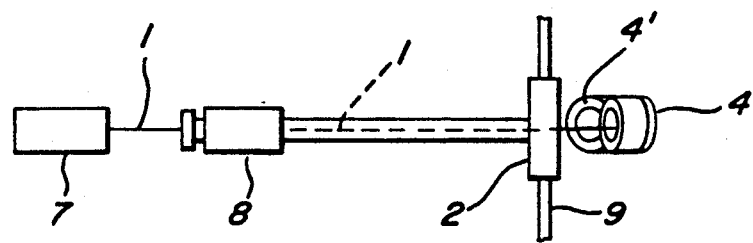
FIG. 1A is a block diagram showing an apparatus for measuring particle size distribution utilizing the preferred embodiment of the invention.
Figure 1B:
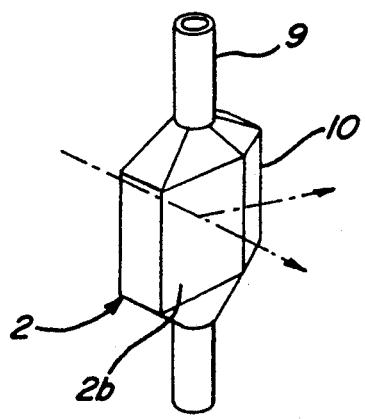
FIG. 1B is a perspective view of a sample cell constructed according to the preferred embodiment of the present invention.
Figure 2:
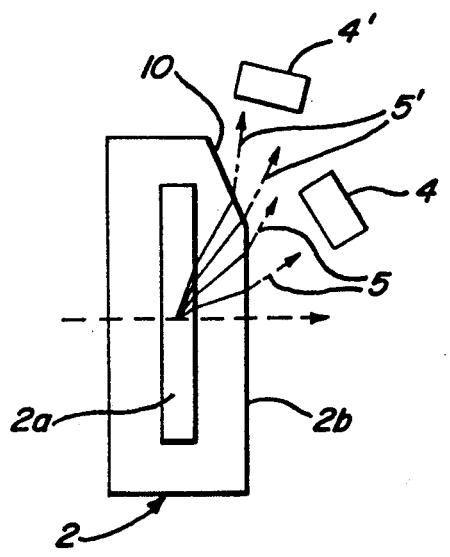
FIG. 2 is a cross-sectional view of the sample cell shown in FIG. 1B.

FIGS. 1A, 1B, and 2 show a preferred embodiment of the present invention. As shown in FIG. 1A, a laser device 7 projects a laser beam 1 through a beam expander 8 for magnifying and conditioning the laser beam 1. The conditioned laser beam 1 is then directed to a sample cell 2.

The sample cell 2 is connected with an ultrasonic disbursion bath (not shown) through a piping 9, allowing the sample cell 2 to be continuously supplied with the sample liquid by a circulating pump (not shown). Detectors 4, 4' are positioned at the rear, exit, or radiating surface of the sample cell 2 for detecting and measuring light which passes through the sample cell 2 and has been diffracted-scattered by the particulates contained within the sample.

As shown in FIG. 1B, the sample cell 2 used in the preferred embodiment of the present invention is provided with a beveled portion 10 formed into the rear exit, or radiating outer surface 2b. Since the light is directed into the first surface of the sample cell 2, the light is transmitted through, and radiates or emerges from, the rear outer surface 2b and is projected onto the detectors 4, 4'.

In the preferred embodiment of the invention, the sample cell 2 is constructed of a material which is transmissive to light. This material may be glass such as quartz or BK-7 glass. The sample cell has a square external cross-section and an internal space 2a as shown in FIG. 2. The beveled portion 10 may be formed in one edge of the outer surface 2b on the radiating side of the sample cell 2 to substantially increase the angle. The scattered light 5' is incident upon the radiating surface by providing the beveled portion 10. The beveled portion 10 allows the scattered light 5' to be transmitted through the rear surface of the sample cell 2 at the beveled portion 10 and thereby impinge on detector 4'.

Additionally, scattered light 5 having small scattering angles will pass directly through the outer surface 2b of the sample cell 2 at a point which is not beveled and will thereby be detected by detector 4.

A collecting lens may also be placed behind the sample cell 2 to collect both scattered light 5 emanating from the outer surface 2b of the sample cell 2 and scattered light 5' emanating from the beveled portion 10, the collecting lens focusing both components of the scattered light upon a single detector.

Figure 3:
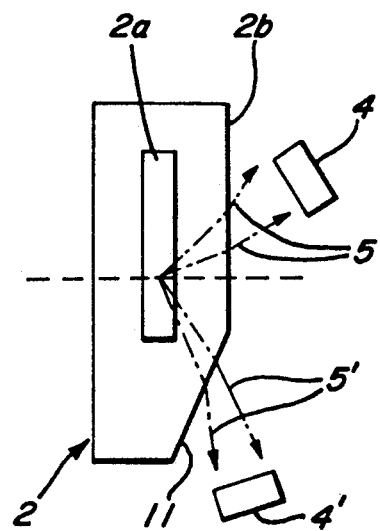
FIG. 3 shows a cross-sectional view of a second preferred embodiment of the present invention and the operation of a sample cell.
Figure 4:
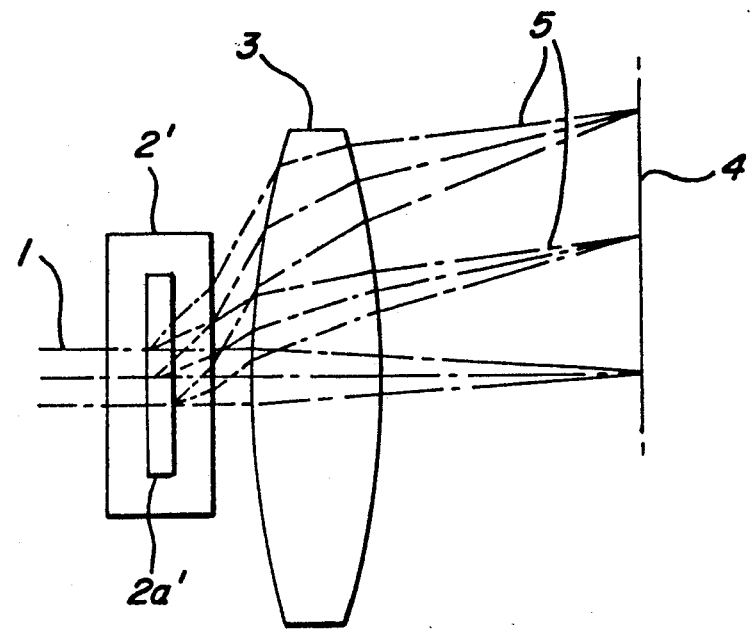
FIG. 4 shows a conventional apparatus for making diffraction measurements of particle size distributions.
Figure 5A:
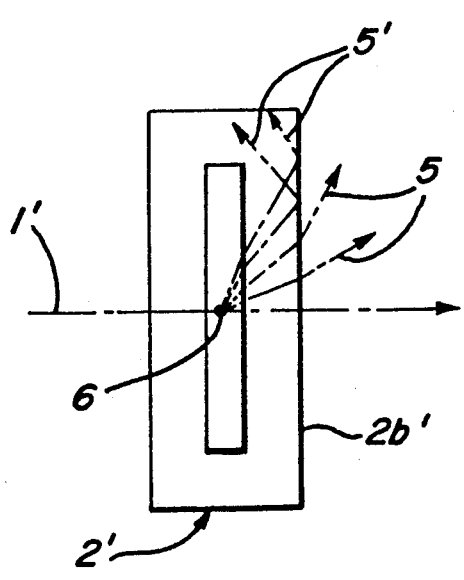
FIG. 5A shows the operation of the sample cell utilized in the apparatus depicted in FIG. 4.
Figure 5B:
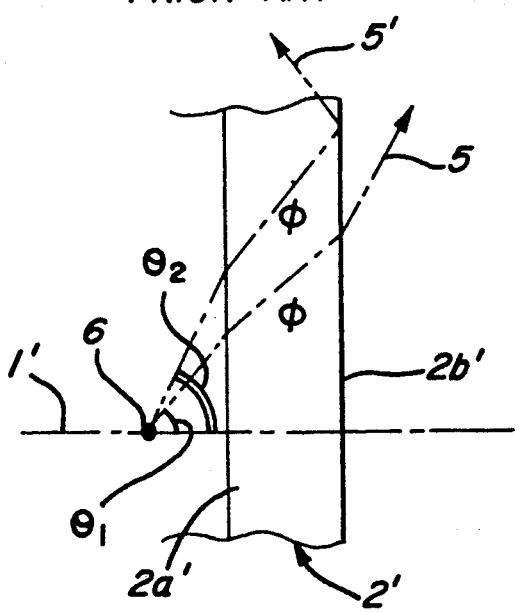
FIG. 5B shows the interaction of scattered light within the sample cell of FIG. 5A.

FIG. 3 shows a sample cell 2 constructed according to an additional preferred embodiment of the present invention. A sample cell 2 is provided with a beveled portion 11 formed in an edge portion opposite to that used in the preferred embodiment shown in FIG. 2. A detector 4' is used to detect the scattered light 5' emanating through the beveled portion 11. Detector 4 measures the scatted light 5 emanating through the outer surface 2b.

The angles of the beveled portions 10, 11 shown in the preferred embodiment illustrated in FIGS. 1, 2, and 3 are configured differently, depending upon the material and size of the sample cell and the other transmissive characteristics of the sample cell and the medium being measured. In addition, the beveled portions 10, 11 may have either a curve or other geometry to allow simplified light transmission, the straight beveled portion being illustrated merely for ease of operation and explanation.

Thus, according to the preferred embodiment of the present invention, the particle size distribution of particulates within a sample ranging from small particle diameters to large particle diameters may be more accurately measured by a simplified device wherein a beveled portion is formed into the outer surface of the sample cell.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An apparatus for making diffraction-scattering measurement of a particle size distribution of a sample, comprising:
   a sample cell for allowing a liquid containing particulates to flow through an internal space of the sample cell, the sample cell being irradiated by a light beam, said light beam entering said sample cell through an entrance surface of said sample cell;
   the light component being diffracted-scattered by the particulates to produce an intensity pattern, the intensity pattern emerging through an exit surface of the sample cell, and
   optical detector means operatively positioned for detecting said intensity pattern emerging from said exit surface;
   the exit surface having at least two portions, said portions being beveled with respect to each other to provide increased transmission of the diffracted/scattered light pattern to the detector, one of said portions being perpendicular to the beam.

2. The apparatus of claim 1 wherein the internal space of the sample cell is connected to piping for allowing the liquid to continuously flow through the sample cell.

3. The apparatus of claim 2 wherein the piping is connected to a n ultrasonic disbursion bath through which the liquid is pumped by a circulating pump.

4. The apparats of claim 1 wherein the light beam is supplied by a laser.

5. The apparatus of claim 4 wherein the light beam supplied by the laster is magnified and conditioned prior to irradiating the sample cell.

6. The apparatus of claim 1 wherein the sample cell is constructed of a light transmissive material.

7. The apparatus of claim 6 wherein the light transmissive material is glass.

8. The apparatus of claim 6 wherein the light transmissive material is quartz.

9. The apparatus of claim 6 wherein the light transmissive material is BK-7 glass.

10. The apparats of claim 1 wherein the sample cell has a generally rectangular external cross-section wherein the exit surface of the sample cell is beveled to eliminate one corner of the cell's square external cross-section.

11. The apparatus of claim 1 wherein the exit surface of the sample cell is beveled such that the scattered light component is incident upon the external surface of the sample cell is at an angle to eliminate reflection of the diffracted component form the external surface.

12. A sample cell for use in diffraction-scattering measurements of particle size distributions of a sample containing particulates, wherein the sample cell accepts an incident light beam and has an exit surface from which an intensity pattern provided by the light beam emerges, said exit surface having at least two portions beveled with respect to each other, the beveled portions allowing light diffracted/scattered by particulates within said sample cell to be transmitted through the exit surface to a detector, steeply scattered portion of said light beam passing through at least one portion which is not perpendicular to the incident beam, and wherein at least one portion is perpendicular to the light beam to allow diffracted light to be measured.

13. An apparatus for making diffraction-scattering measurements of particle size distribution of a sample, comprising:

means for providing a beam of light along an optical axis;

a sample cell for containing a sample having particulates suspended in a liquid, said sample cell having an entrance surface and an exit surface, said entrance surface receiving said beam of light, said particulates being of sizes sufficient to diffract-scatter portions of said beam of light to produce an exit beam having an intensity pattern, said exit beam emerging from said sample cell through said exit surface at diffraction/scattering angles determined by the size of the particles;

said ext surface comprising at least first and second planar surfaces angled with respect to each other, with at least one of said planar surfaces being perpendicular to said optical axis, and with a first portion of said exit beam emerging through sad first planar surface and a second portion of said exit beam emerging through said second planar surface; and an optical detector means for detecting said intensity pattern emerging from said exit aperture, said optical detector means having at least first and second detectors with sad first detector receiving light emerging from said sample cell from said first planar surface and said second optical detector receiving light emerging from said sample cell from said second planar surface.

14. The apparats of claim 13, wherein said first and second planar surfaces are joined along a substantially linear edge, said edge being disposed through and normal to said optical axis, said first and second planar surfaces being oriented at equal angles from said optical axis.

15. The apparatus of claim 13, wherein said first and second planar surfaces are joined along a substantially linear edge, said edge being offset from said optical axis, said first planar surface being oriented perpendicular to said optical axis, said second planar surface being oriented at an angle with respect to said first planar surface.

* * * * *